United States Patent [19]

Tanaka et al.

[11] Patent Number: 4,826,959

[45] Date of Patent: May 2, 1989

[54] 2,2'-AZOBIS(2,4-DIMETHYLVALERONI-TRILE) ISOMER MIXTURE PREDOMINANT IN LOW MELTING ISOMER AND HAVING HIGH SOLUBILITY

[75] Inventors: Motoaki Tanaka, Urawa; Tsutomu Miyagawa; Hideo Takeuchi, both of Kawagoe, all of Japan

[73] Assignee: Wako Pure Chemical Industries, Ltd., Osaka, Japan

[21] Appl. No.: 150,264

[22] Filed: Jan. 29, 1988

Related U.S. Application Data

[63] Continuation of Ser. No. 491,385, May 4, 1983, abandoned.

[30] Foreign Application Priority Data

Feb. 26, 1983 [JP] Japan .................................. 58-31240

[51] Int. Cl.$^4$ .................. C07C 107/00; C07C 107/02; C07C 107/04
[52] U.S. Cl. .................................... 534/838; 252/350; 526/218; 526/218.1; 526/260; 526/263; 526/291; 526/317; 526/328; 526/330; 526/341; 526/343; 526/344; 526/338; 526/352; 534/573; 534/887
[58] Field of Search ........................ 534/838; 252/350; 526/218.1, 218, 260, 263, 291, 217, 328, 330, 341, 343, 344, 338, 352

[56] References Cited

U.S. PATENT DOCUMENTS

| | | | |
|---|---|---|---|
| 2,469,358 | 5/1949 | Alderson et al. | 534/838 X |
| 2,492,763 | 12/1949 | Pinkney | 534/838 |
| 3,959,343 | 5/1976 | Arashi et al. | 534/838 |
| 3,987,025 | 10/1976 | Moore | 534/838 |
| 4,272,435 | 6/1981 | Matsuda et al. | 534/838 |
| 4,315,856 | 2/1982 | Moore | 534/838 |

FOREIGN PATENT DOCUMENTS 76731827 11/1976 Japan .................................. 534/838

OTHER PUBLICATIONS

Lewis et al., J. Amer. Chem. Soc., vol. 71, pages 747 and 748 (1949).
Overberger et al. I, J. Amer. Chem. Soc., vol. 73, pages 2618 to 2621 (1951).
Overberger et al. II, J. Amer. Chem. Soc., vol. 71, pages 2661 to 2666 (1949).

*Primary Examiner*—Floyd D. Higel
*Attorney, Agent, or Firm*—Armstrong, Nikaido, Marmelstein & Kubovcik

[57] ABSTRACT

A mixture of an isomer of 2,2'-azobis(2,4-dimethylvaleronitrile) having a low melting point in an amount of about 70% by weight or more and an isomer of 2,2'-azobis(2,4-dimethylvaleronitrile) having a high melting point in an amount of about 30% by weight or less shows excellent solvent solubility, which is higher than that of the isomer having a low melting point. The mixture is useful as a polymerization initiator, and also as a blowing agent.

4 Claims, 2 Drawing Sheets

2,2'-AZOBIS(2,4-DIMETHYLVALERONITRILE) ISOMER MIXTURE PREDOMINANT IN LOW MELTING ISOMER AND HAVING HIGH SOLUBILITY

This is a continuation of application Ser. No. 491,385, filed May 4, 1983, and now abandoned.

BACKGROUND OF THE INVENTION

This invention relates to a mixture of isomers of 2,2'-azobis(2,4-dimethylvaleronitrile) (hereinafter referred to as "ADVN") having greater solvent solubility than an isomer of ADVN having a low melting point.

ADVN is useful as a radical polymerization initiator, blowing agent and the like. It is particularly useful as polymerization initiator for vinyl chloride and acrylonitrile and also widely useful as polymerization initiator for polymerizable unsaturated monomers such as ethylene, styrene, acrylic acid esters, methacrylic acid esters, vinyl fluoride, vinyl acetate, acrylamide, acrylic acid, methacrylic acid, vinyl pyridine, and the like.

It is known that ADVN has two isomers, one of which is a meso-form having a melting point as low as 56° C. to 57° C., i.e. a low melting point isomer (hereinafter referred to as "LMP"). The other isomer is a dl-form having a melting point as high as 74° C. to 77° C., i.e. a high melting point isomer (hereinafter referred to as "HMP") as reported in J. Am. Chem. Soc., vol. 73, pages 2618–2621 (1951) by C. G. Overberger.

The mixing ratio of the two isomers can be controlled to some extent by selecting manufacturing methods in industrial production (Japanese Patent Appln Kokai (Laid-Open) No. 131827/76).

Commercially available ADVN is LMP only or HMP only or a mixture of HMP and LMP in about a 1:1 mixing ratio (by weight).

As to solvent solubility of the two isomers of ADVN, it is known that the solubility of LMP is several times higher than that of HMP and of a commercially available 1:1 mixture of LMP and HMP. Thus, it has been believed that if ADVN containing only LMP can be produced, this ADVN would present advantages over the conventional mixture in terms of polymerization activity and selection of solvent used for polymerization; these properties are very important for a new polymerization initiator.

The present inventors have studied the solvent solubility of ADVN containing LMP and HMP in various mixing ratios, investigated undesirable influences on the solvent solubility of ADVN, find that a special mixture of HMP and LMP has higher solvent solubility than LMP alone and accomplished this invention.

SUMMARY OF THE INVENTION

The objects of this invention are to provide a mixture of isomers of ADVN having higher solvent solubility than LMP alone, and a process for producing the same.

This invention provides a mixture of an isomer of 2,2'-azobis(2,4-dimethylvaleronitrile) having a low melting point in an amount of less than 100% by weight to about 70% by weight and an isomer of 2,2'-azobis(2,4-dimethylvaleronitrile) having a high melting point in an amount of more than zero to about 30% by weight.

DESCRIPTION OF PREFERRED EMBODIMENTS

As to the solvent in which the mixture of ADVN isomers is to be dissolved, there is no particular limit thereto so long as it is an organic solvent and it can be used in polymerization initiated by the mixture of ADVN isomers of this invention. Examples of the organic solvent are methanol, toluene, hexane, mineral spirits, Methyl Cellosolve, dichloroethane, dimethyl sulfoxide, dimethylformamide, etc.

As the organic solvent, it is also possible to use polymerizable organic monomers such as vinyl chloride, vinyl acetate, styrene, acrylic acid, methacrylic acid, methyl acrylate, ethyl acrylate, isopropyl acrylate, n-butyl acrylate, hydroxyethyl acrylate, methyl methacrylate, ethyl methacrylate, isopropyl methacrylate, n-butyl methacrylate, hydroxyethyl methacrylate, acrylonitrile, and the like.

Figure 1:
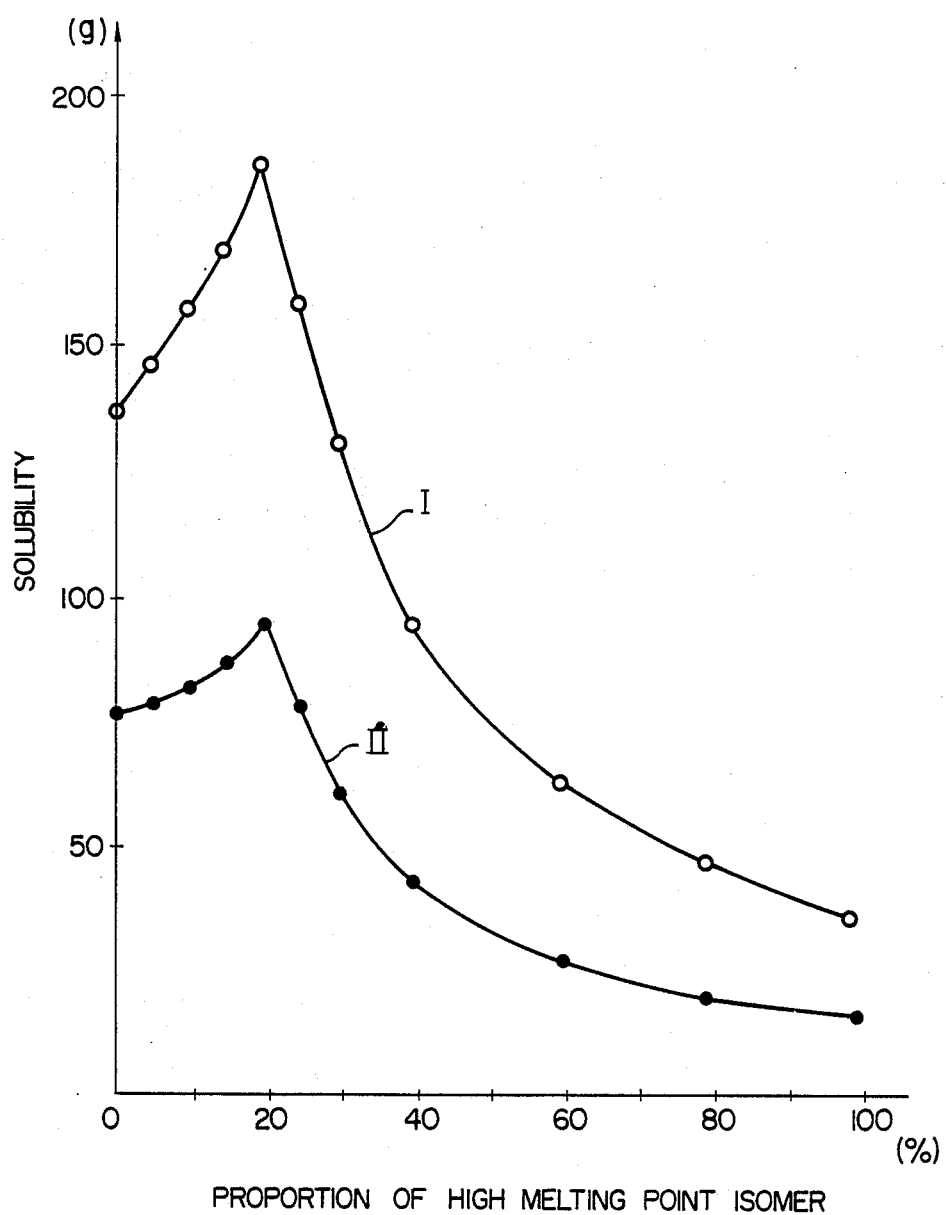
FIGS. 1 and 2 are graphs showing the relationship between solubility and the proportion of the high melting point isomer (HMP) in the mixture.
Figure 2:
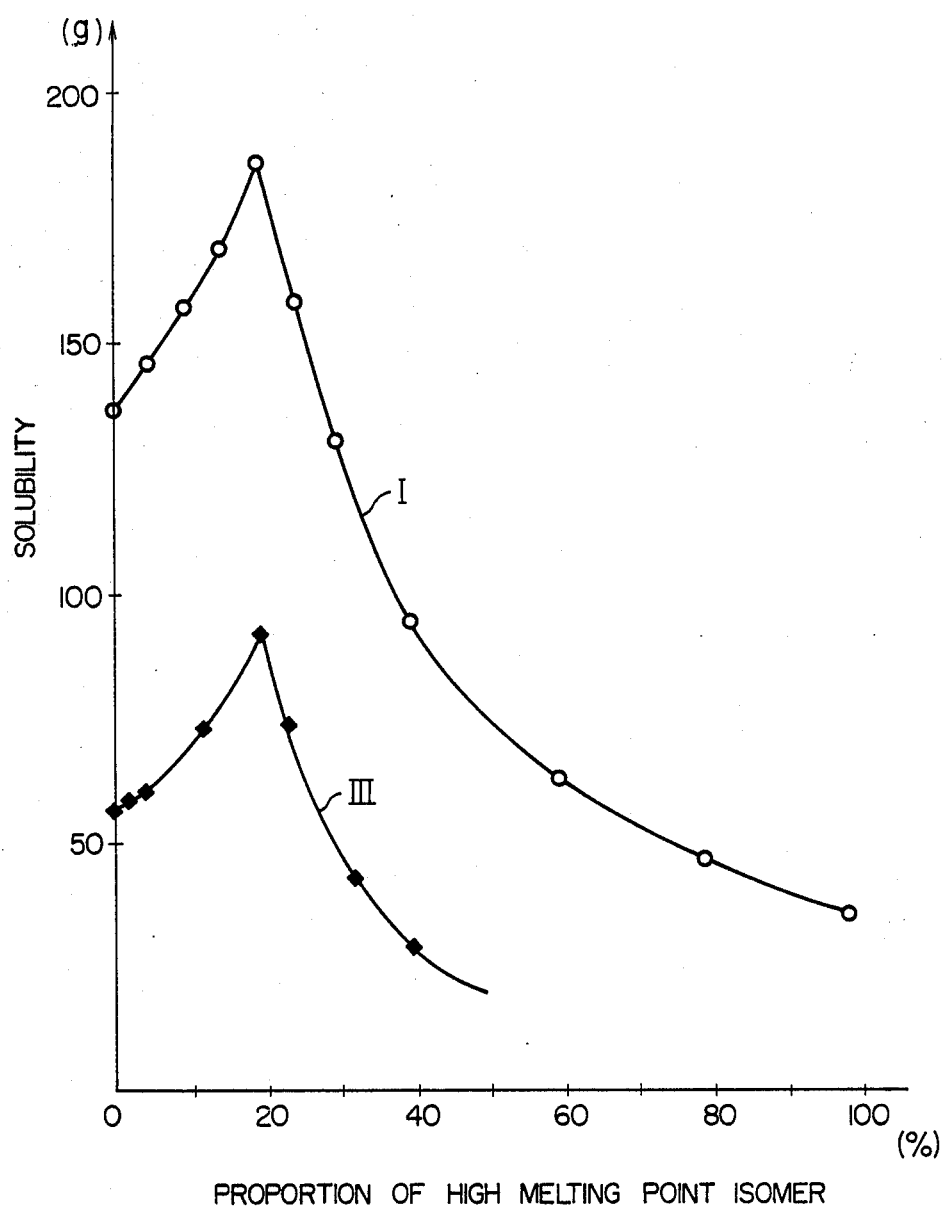

In other words, the solvent solubility of the mixture of ADVN isomers of this invention is not influenced by the kind of organic solvent used and shows a special pattern as shown in the attached FIGS. 1 and 2. Further, said special pattern of the solubility curve is not influenced by temperature as shown in FIG. 1.

It should be noted that such special features of the solvent solubility of the mixture of ADVN isomers of this invention cannot be obtained with HMP alone or with LMP alone, but can only be obtained by adding a special amount of HMP (which has poorer solvent solubility than to LMP) in a special amount.

In the mixture of ADVN isomers of this invention, HMP should be more than zero to about 30% by weight, preferably 8% by weight or more, particularly about 10% by weight or more and about 25% by weight or less, and LMP should be less than 100% by weight and about 70% by weight or more, preferably 92% by weight or less, particularly about 90% by weight or less and about 75% by weight or more. If the amounts of HMP and LMP are outside the above-mentioned ranges, solvent solubility undesirably decreases as shown in FIGS. 1 and 2. The most preferable range is about 15 to 23% by weight of HMP and about 85 to 77% by weight of LMP.

The mixture of ADVN isomers of this invention can be obtained by mixing HMP with LMP by conventional mixing processes. For example, there is disclosed in Japanese Patent Appln Kokai (Laid-Open) No. 131827/76 a process for producing LMP having a purity of 93% to 98%, wherein 2,2'-hydrazobis(2,4-dimethylvaleronitrile) (a hydrazo form of ADVN) is reacted with hydrogen cyanide for a long period of time in the presence of hydrogen cyanide to give a hydrazo form which can produce LMP. Highly pure LMP can easily be produced by this process. To the resulting LMP, a suitable amount of HMP is added.

LMP, and if necessary HMP, can be isolated by fractional recrystallization and used for preparing the mixture of ADVN isomers of this invention. Further, a commercially available 1:1 mixture of HMP and LMP can be used for preparing the mixture of ADVN isomers of this invention.

The resulting mixture of LMP and HMP is usually in the form of crystals.

The mixture of ADVN isomers of this invention has higher solvent solubility than LMP alone (which is higher than the solubility of a 1:1 mixture of LMP and HMP, or HMP alone) and has particular advantages as polymerization initiator. Further, since the amount of solvent for dissolving ADVN can be reduced remarkably when the mixture of ADVN isomers of this invention is used as polymerization initiator, the resulting polymer shows excellent physical and chemical properties, the production cost is lowered remarkably and working conditions can be improved remarkably. Such effects cannot be expected from the sole use of LMP.

This invention is illustrated by way of the following Examples in which all parts and percents are by weight unless otherwise specified. Further, the amounts of HMP and LMP are measured and determined by infrared absorption spectra and the intensities of individual characteristic absorptions.

Example 1

HMP (m.p. 77.5°–79.5° C.) and LMP (m.p. 57.5°–59.0° C.) obtained by fractional recrystallization of commercially available ADVN were mixed in predetermined amounts to give mixtures as listed in Table 1. Each mixture was placed in 100 parts of toluene and the amount of the mixture dissolved at 5° C. (curve II in FIG. 1) and 20° C. (curve I in FIG. 1) was measured and listed in Table 1 and plotted in FIG. 1 to show solubility curves.

As shown in Table 1 FIG. 1, the mixtures containing HMP in proportion of 5% to 25% show better solubility than LMP alone. Further, the solubility curves show the same pattern at both dissolving temperatures of 5° C. and 20° C.

TABLE 1

| Run No. | Composition of mixture | | Dissolved amount in toluene (parts) | |
|---|---|---|---|---|
| | HMP (%) | LMP (%) | 5° C. | 20° C. |
| 1 | 0 | 100 | 78 | 139 |
| 2 | 5 | 95 | 80 | 148 |
| 3 | 10 | 90 | 83 | 159 |
| 4 | 15 | 85 | 88 | 171 |
| 5 | 20 | 80 | 96 | 188 |
| 6 | 25 | 75 | 80 | 160 |
| 7 | 30 | 70 | 62 | 132 |
| 8 | 40 | 60 | 44 | 96 |
| 9 | 60 | 40 | 28 | 64 |
| 10 | 80 | 20 | 21 | 48 |
| 11 | 100 | 0 | 17 | 37 |

Example 2

Commericially available ADVN (a mixture of HMP and LMP in 40:60 weight ratio) was mixed with LMP (m.p. 57.5°–59.0° C.) in predetermined amounts to give mixtures as listed in Table 2. Each mixture was placed in 100 parts of methanol and the amount of the mixture dissolved at 20° C. was measured and listed in Table 2 and plotted in FIG. 2 (the curve III). In FIG. 2, the curve I is also shown for comparison.

As shown in Table 2 and FIG. 2, the mixtures containing HMP in proportion of 2% to 24% show better solubility than LMP alone. Further, the solubility curves show the same pattern in both cases of toluene and methanol.

TABLE 2

| Run No. | Mixing ratio (%) | | Composition of mixture | | Dissolved amount in methanol (parts) |
|---|---|---|---|---|---|
| | Commercially available ADVN | LMP | HMP (%) | LMP (%) | |
| 1 | 0 | 100 | 0 | 100 | 57 |
| 2 | 5 | 95 | 2 | 98 | 59 |
| 3 | 10 | 90 | 4 | 96 | 61 |
| 4 | 30 | 70 | 12 | 88 | 74 |
| 5 | 50 | 50 | 20 | 80 | 93 |
| 6 | 60 | 40 | 24 | 76 | 75 |
| 7 | 80 | 20 | 32 | 68 | 43 |
| 8 | 100 | 0 | 40 | 60 | 29 |

What is claimed is:

1. A mixture consisting of about 85% to about 77% by weight of an isomer of 2,2'-azobis-(2,4-dimethylvaleronitrile) having a low melting point and about 15% to about 23% by weight of an isomer of 2,2'-azobis(2,4-dimethylvaleronitrile) having a high melting point.

2. A mixture consisting of about 80% by weight of an isomer of 2,2'-azobis-(2,4-dimethylvaleronitrile) having a low melting point and about 20% by weight of an isomer of 2,1'-azobis(2,4-dimethylvaleronitrile) having a high melting point.

3. A mixture consisting of about 85% to about 77% by weight of an isomer of 2,2'-azobis-(2,4-dimethylvaleronitrile) having a low melting point and about 5% to about 3% by weight of an isomer of 2,2'-azobis(2,4-dimethylvaleronitrile) having a high melting point, said mixture being obtained by mixing (a) 2,2'-azobis(2,4-dimethylvaleronitrile) consisting of about 93% to about 98% by weight of an isomer thereof having a low melting point and about 7% to about 2% of an isomer thereof having a high melting point with (b) an isomer of 2,2'-azobis(2,4-dimethylvaleronitrile) having a high melting point.

4. A mixture consisting of about 85% to about 77% by weight of an isomer of 2,2'-azobis-(2,4-dimethylvaleronitrile) having a low melting point of 57.5° C. to 59.0° C. and 5% to 23% by weight of an isomer of 2,2'-azobis(2,4-dimethylvaleronitrile) having a high melting point of 77.5° to 79.5° C., said mixture being obtained by mixing said isomer of 2,2'-azobis(2,4-dimethylvaleronitrile) having the high melting point with said isomer of 2,2'-azobis(2,4-dimethylvaleronitrile) having the low melting point.

* * * * *